(12) United States Patent
Beckert et al.

(10) Patent No.: US 11,702,697 B2
(45) Date of Patent: Jul. 18, 2023

(54) QUALITY TESTING OF DNA SAMPLES

(71) Applicant: Roche Sequencing Solutions, Inc., Pleasanton, CA (US)

(72) Inventors: Sophie Beckert, Neuzelle (DE); Bernd Hinzmann, Penzberg (DE)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

(21) Appl. No.: 17/055,038

(22) PCT Filed: May 14, 2018

(86) PCT No.: PCT/EP2018/062304
§ 371 (c)(1),
(2) Date: Nov. 12, 2020

(87) PCT Pub. No.: WO2019/219157
PCT Pub. Date: Nov. 21, 2019

(65) Prior Publication Data
US 2021/0214790 A1 Jul. 15, 2021

(51) Int. Cl.
C12Q 1/68 (2018.01)
C12Q 1/6876 (2018.01)
C12Q 1/6848 (2018.01)
C12Q 1/6851 (2018.01)

(52) U.S. Cl.
CPC ......... C12Q 1/6876 (2013.01); C12Q 1/6848 (2013.01); C12Q 1/6851 (2013.01)

(58) Field of Classification Search
CPC ....................................................... C12Q 1/68
USPC ............................................................ 435/6
See application file for complete search history.

(56) References Cited

U.S. PATENT DOCUMENTS

| 2014/0051075 A1 | 2/2014 | Sinha |
| 2014/0274734 A1 | 9/2014 | Wang et al. |
| 2016/0186239 A1* | 6/2016 | Sinha ............... C12Q 1/6851 506/9 |

FOREIGN PATENT DOCUMENTS

WO   WO-2010014920 A1 * 2/2010 ........... C12Q 1/6886

OTHER PUBLICATIONS

Livak et al, Analysis of relative gene expression data using real-time quantitative PCR and the 2(-Delta Delta C(T)) Method. Dec. 2001;25(4):402-8. doi: 10.1006/meth.2001.1262.*
Livak et al., Analysis of relative gene expression data using real-time quantitative PCR and the 2(-Delta Delta C(T)) Method, Methods. Dec. 2001;25(4):402-8. doi: 10.1006/meth.2001.1262.*

(Continued)

*Primary Examiner* — Aaron A Priest
(74) *Attorney, Agent, or Firm* — Pamela C. Ancona; Olga Kay

(57) ABSTRACT

The present invention provides method essentially comprising the steps of (i) providing a DNA sample, (ii) providing at least a first pair of amplification primers which is capable of generating a first amplicon from a LINE sequence that has a size of less than 80 bp, (iii) providing at least a second pair of amplification primers which is capable of generating a second amplicon from a LINE sequence that has a size of more than 160 bp, (iv) performing a qPCR and determining cq values for each of the generated amplicons, and (v) determining the relative concentrations of said amplicons.

4 Claims, 1 Drawing Sheet
Specification includes a Sequence Listing.

Priming sites and amplifiable PCR fragments in low quality DNA

(56) References Cited

OTHER PUBLICATIONS

Mead et al., Circulating tumour markers can define patients with normal colons, benign polyps, and cancers, Br J Cancer. Jul. 12, 2011;105(2):239-45. doi: 10.1038/bjc.2011.230. Epub Jun. 28, 2011.*

Madhaven et al., Plasma DNA integrity as a biomarker for primary and metastatic breast cancer and potential marker for early diagnosis, Breast Cancer Res Treat. Jul. 2014;146(1):163-74. doi: 10.1007/s10549-014-2946-2. Epub May 17, 2014.*

International Search Report and Written Opinion for PCT/EP2018/062304, dated Jun. 22, 2018.

Madhavan D. et al, Plasma DNA integrity as a biomarker for primary and metastatic breast cancer and potential marker for early diagnosis, Breast Cancer Res Treat, (2014), pp. 163-174, vol. 146, Issue 1.

Sunami E. et al, Quantification of LINE1 in Circulating DNA as a Molecular Biomarker of Breast Cancer, Annals of the New York Academy of Science, (2008), pp. 171-174, vol. 1137 Issue 1.

* cited by examiner

SEQUENCE LISTING

<160> NUMBER OF SEQ ID NOS: 5

<210> SEQ ID NO 1
<211> LENGTH: 18
<212> TYPE: DNA
<213> ORGANISM: Artificial Sequence
<220> FEATURE:
<223> OTHER INFORMATION: synthetic oligonucleotides

<400> SEQUENCE: 1
ttgcggaagt cagtgtgg         18

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotides

<400> SEQUENCE: 2
gatggctggg tcaaatggta         20

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotides

<400> SEQUENCE: 3
acttggaacc aacccaaatg         20

<210> SEQ ID NO 4
<211> LENGTH: 20

```
<212> TYPE: DNA
<213> ORGANISM: Artificial Sequence
<220> FEATURE:
<223> OTHER INFORMATION: synthetic oligonucleotides

<400> SEQUENCE: 4
tgagaatatg cggtgtttgg                                              20

<210> SEQ ID NO 5
<211> LENGTH: 22
<212> TYPE: DNA
<213> ORGANISM: Artificial Sequence
<220> FEATURE:
<223> OTHER INFORMATION: synthetic oligonucleotides

<400> SEQUENCE: 5
caaacaaccc catcaaaaag tg                                           22
```

QUALITY TESTING OF DNA SAMPLES

CROSS-REFERENCE TO RELATED APPLICATIONS

This application is a national stage of the International Application Ser. No. PCT/EP2018/062304 filed of May 14, 2018, and claims priority to the European application Serial No. 17171576.6 files on May 17, 2017. All of the above applications are incorporated herein by reference.

FIELD OF INVENTION

The present invention is directed to the design and use of a LINE qPCR assay. It is designed in order to determine the concentration of little amounts of DNA typically obtained after the extraction of cell free DNA from plasma or DNA from FFPET biopsies.

BACKGROUND OF THE INVENTION

Genotyping of tumor tissues at diagnosis is useful to guide proper therapy selection. Most commonly, this genotyping of the tumor is performed using a slide or curl from a tissue biopsy that has been fixed in formalin and embedded in paraffin (i.e., formalin fixed paraffin embedded tissue, or FFPET). However, the process of fixation and embedding, as well as storage of these FFPET samples (potentially for decades) generally leads to chemical damage of the DNA. This damage makes correct identification of tumor-specific variants more difficult, both by increasing the "noise" due to errors created by damaged DNA, as well as decreasing the "signal" by rendering processing of the FFPET-derived DNA with standard molecular biology techniques less efficient than the processing of other types of DNA using the same or similar techniques. In addition, isolation of DNA from FFPET samples is typically a time-consuming process that uses reagents such as xylene which can require additional safety precautions. Moreover, the isolation process can result in highly variable quantities of DNA that are of variable quality.

The state of the art method for determining the quality of DNA samples and in particular FFPET samples is the hgDNA quantification Kit and QC kit from KAPABIOSYSTEMS. The kit amplifies 3 targets of different lengths within a conserved single-copy locus in the human genome. Normalization of the concentrations of the longer amplicons to the shorter amplicon is calculated for quality, termed "Q-ratio". Samples consisting of high-quality DNA without single strand or double strand breaks will result in Q-ratios close to 1, while damaged DNA will result in poorer amplification of the longer amplicon and thus in Q-ratios significantly less than 1. However, measurement of samples with low DNA concentration is instable and imprecise (high cq-error). For reliable measurements higher amounts of DNA are needed, which are often not available for clinical samples such as fine needle biopsies.

BRIEF DESCRIPTION OF THE INVENTION

Thus, the present invention is directed to a method comprising the steps of
a) providing a DNA sample,
b) providing at least a first pair of amplification primers which is capable of generating a first amplicon from a human LINE sequence that has a size of less than 80 bp,
c) providing at least a second pair of amplification primers which is capable of generating a second amplicon from a LINE sequence that has a size of more than 160 bp,
d) performing a qPCR and determining cq values for each of the generated amplicons, and
e) determining the relative concentrations of said amplicons In one embodiment, the inventive method further comprises the step of b'), providing at least a third pair of amplification primers which is capable of generating a third amplicon from a LINE sequence that has a size of more than 300 bp. The cq values obtained may be normalized by means of using a calibrator sample in such a way that steps a) to e) are performed on said sample and said calibrator sample in parallel.

In one embodiment, one, two or all primer pairs are selected from a group consisting of a primer pair according to SEQ ID. No: 1 and 2, a primer pair according to SEQ ID No: 3 and 4, and a primer pair according to SEQ ID NO: 5 and 2.

The relative concentrations determined according to the inventive methods may represent a measure for the quality of the analyzed DNA sample. This is of particular importance, if the sample is an FFPET (formalin fixed and paraffin embedded tissue) sample.

The sample may also be a cell free DNA sample. In this case, said relative concentrations are indicative for the contamination of said cell free DNA with cellular DNA. This is possible due to the fact that cellular DNA is less degraded as compared to cell free DNA.

In a further aspect, the present invention provides a kit comprising at several or all of the following primer pairs:
a primer pair according to SEQ ID. No: 1 and 2
a primer pair according to SEQ ID No: 3 and 4, and
a primer pair according to SEQ ID NO: 5 and 2

DETAILED DESCRIPTION OF THE INVENTION

Definitions

Figure 1:
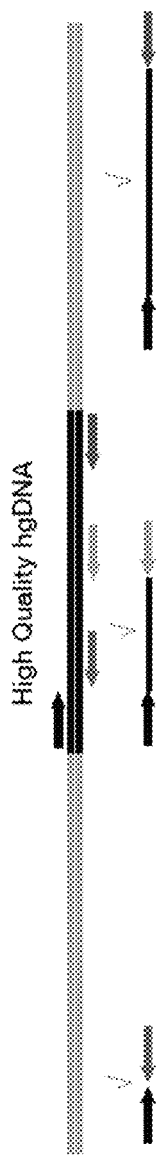
FIG. 1 schematically shows priming sites and amplifiable PCR fragments in high quality DNA FIG. 2 schematically shows priming sites and amplifiable PCR fragments in low quality DNA

The term "sample", as used herein, refers to a material suspected of containing a DNA of interest. The sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid, tissue, cells or the like. The test sample can be pretreated prior to use, such as preparing plasma from blood, diluting viscous fluids, lysis or the like; methods of treatment can involve filtration, distillation, concentration, inactivation of interfering components, and the addition of reagents. A sample may be used directly as obtained from the source or following a pretreatment to modify the character of the sample, e.g. after being diluted with another solution or after having being mixed with reagents e.g. to carry out one or more diagnostic assays The term "sample" as used herein is therefore not only used for the original sample but also relates to a sample which has already been processed by standard methods well known in the art. In particular, the sample may be a DNA sample that has been enriched, purified, diluted, or mixed with reagents. In a particular embodiment, the sample may be a formalin fixed and paraffin embedded tissue sample (FFPET sample) from which total nucleic acid or DNA has been isolated. In another particular embodiment, the sample may be cell free DNA that has been isolated from human blood, serum or plasma.

The terms "template nucleic acid", "template molecule", "target nucleic acid", and "target molecule" can be used interchangeably and refer to a nucleic acid molecule that is the subject of an amplification reaction that may optionally be interrogated by a sequencing reaction in order to derive its sequence information. The terms "template specific region", "target specific region" or "region of interest" can be used interchangeably and refer to the region of a particular nucleic acid molecule that is of scientific interest. These regions typically have at least partially known sequences in order to design primers which flank the region or regions of interest for use in amplification reactions and thereby recover target nucleic acid amplicons containing these regions of interest.

The term "oligonucleotide" refers to a nucleic acid that includes at least two nucleic acid monomer units (e.g., nucleotides). An oligonucleotide typically includes from about six to about 175 nucleic acid monomer units, more typically from about eight to about 100 nucleic acid monomer units, and still more typically from about 10 to about 50 nucleic acid monomer units (e.g., about 15, about 20, about 25, about 30, about 35, or more nucleic acid monomer units). The exact size of an oligonucleotide will depend on many factors, including the ultimate function or use of the oligonucleotide.

The term "primer" further relates to such oligonucleotides which are used in amplification reactions and anneal to a target sequence. Common modifications of primers include modification of the 3' nucleotides to prevent unspecific amplification products such as primer dimers. Such modifications are well known in the art and include, as non-limiting examples, t-Butyl benzyl-dA or -Butyl benzyl-dC. Such modifications are also included in the term "primer".

The term "amplification" generally refers to the production of a plurality of nucleic acid molecules from a target nucleic acid wherein primers hybridize to specific sites on the target nucleic acid molecules in order to provide an initiation site for extension by a polymerase. Amplification can be carried out by any method generally known in the art, such as but not limited to: standard PCR, long PCR, hot start PCR, qPCR, RT-PCR and Isothermal Amplification. The term "amplicon" generally refers to selected amplification products which are amplified by aDNA polymerase together with a specific set of forward and reverse primers such as those produced from amplification techniques known in the art. The term "pair of amplification primers" refers to a pair of oligonucleotides which together can act as a forward and reverse primer to generate an amplicon from a target DNA.

The term "quantitating" as used herein relates to the determination of the amount or concentration of a target nucleic acid present in a sample. The term "qPCR" generally refers to the PCR technique also known as real-time quantitative polymerase chain reaction, quantitative polymerase chain reaction or kinetic polymerase chain reaction. This technique simultaneously amplifies and quantifies target nucleic acids using PCR wherein the quantification is by virtue of an intercalating fluorescent dye or sequence-specific probes such as TaqMan probes or FRET Hybprobes, which contain fluorescent reporter molecules that are only detectable once hybridized to a target nucleic acid. The term "detecting" as used herein relates to a qualitative test aimed at assessing the presence or absence of a target nucleic acid in a sample.

The term "PCR efficiency" refers to an indication of cycle to cycle amplification efficiency for the perfectly matched primer template. PCR efficiency is calculated for each condition using the equation: % PCR efficiency=(10(-slope)−1)×100, wherein the slope was calculated by linear regression with the log copy number plotted on the y-axis and Cq plotted on the x-axis.

Embodiments of the Invention

The present invention provides a new method for the determination of the quality of a DNA sample. By amplifying targets of different sizes (i.e., sequences having different lengths in nucleotides), an estimate of the extent of degradation of the DNA—and therefore of the quality of the DNA—can be determined. This approach is based on the theory that as a sample becomes increasingly degraded due to DNA damage or the like, fewer copies of the full length sequence targeted by the primers in qPCR experiment will exist, and therefore there will be less likely to result in successful amplification. By leveraging this phenomenon, an estimate of the quality of the DNA can be determined by first measuring the concentrations of differently sized target regions via qPCR in the step 106, and then taking a ratio of the concentration of first (longer) target region to the concentration of a second (shorter) target region in the step 108. The resulting Q-ratio will have a value of 1.0 for a DNA sample with little to no degradation, whereas the Q-ratio will have a value less than 1.0 for a DNA sample exhibiting at least some degradation.

If different concentrations are determined with amplicons of different length the ratio of concentrations obtained by using longer amplicons versus the value obtained for shorter fragments is an indicator for the degradation of the input DNA. For undegraded samples long and short fragments are expected to become amplified in equal amounts. For samples which are partially degraded, or, in other words, which contain single or double stranded DNA breaks distributed randomly all over the genome, the probability for a successful amplification of longer DNA fragments statistically decreases as compared to the amplification of shorter DNA fragments. According to the present invention, it is mandatory to use LINE sequences as a target DNA for the qPCR QC assay. As disclosed above, LINE sequences are sequences that are represented by about 100 000 copies in the human genome. Therefore, such a quality assay using LINE elements as target nucleic acid allows stable standard curves and measurements down to the sub femtogram level. As a consequence, only little material is needed to run the assay. Usually, only 1 µl from the extract is diluted 1:100 and allows thus enough qPCR measurements. With the same approach it is also possible to determine genomic contamination in ctDNA (cell free DNA obtained from blood, serum or plasma). Lysis of blood cells during the separation of plasma by centrifugation leads to increased amounts of larger DNA fragments in the final ctDNA. This will also shift the ratio of concentrations measured by longer versus shorter amplicons.

In the context of the present invention, the template nucleic acid is always the human LINE sequence. LINE is the abbreviation for "long interspersed nuclear elements", also known as "long interspersed nucleotide elements" or "long interspersed elements". These elements are a group of non-LTR retrotransposon elements which constitute about 20% of the human DNA. Each LINE element is about 7000 base pairs long, and there are about 100,000 LINEs copies in the human genome. However, due to the accumulation of random mutations, the sequence of most LINES is degenerated to the extent that they do not act anymore as functional retrotransposon elements.

In one embodiment, particular pairs of amplification primers are used for generating LINE amplicons. The following 3 primer pairs may be used for amplification of a 66 bp fragment, a 191 bp fragment and a 330 bp fragment:

|  |  | Tm |  |
|---|---|---|---|
| 1. LINE 66 bp |  |  |  |
| F: | TTGCGGAAGTCAGTGTGG | 59.9° C. | (SEQ ID No: 1) |
| R: | GATGGCTGGGTCAAATGGTA | 60.4° C. | (SEQ ID No: 2) |
| 2. LINE 191 bp |  |  |  |
| F: | ACTTGGAACCAACCCAAATG | 58.35° C. | (SEQ ID No: 3) |
| R: | TGAGAATATGCGGTGTTTGG | 58.35° C. | (SEQ ID No: 4) |
| 3. LINE 330 bp |  |  |  |
| F: | CAAACAACCCCATCAAAAAGTG | 58.95° C. | (SEQ ID No: 5) |
| R: | GATGGCTGGGTCAAATGGTA | 60.4° C. | (SEQ ID No: 2) |

The use of LINE sequences as target for qPCR overcomes the limitations of other single or multiple copy designs because the sensitivity is highly increased and thus less material for the analysis is required. Choosing LINE sequences as a target is of particular advantage, because LINE sequences are more or less randomly distributed all over the human genome. A respective LINE assay to investigate the degree of DNA damage therefore reflects the quality status of the respective sample all over the complete genome, whereas an analysis of one or more single copy genes only represents the DNA quality of the sample with respect to particular genomic loci. Similarly, analysis of other multi copy genes not randomly distributed all over the genome also does not indicate the quality of the sample as a whole.

Figure 2:
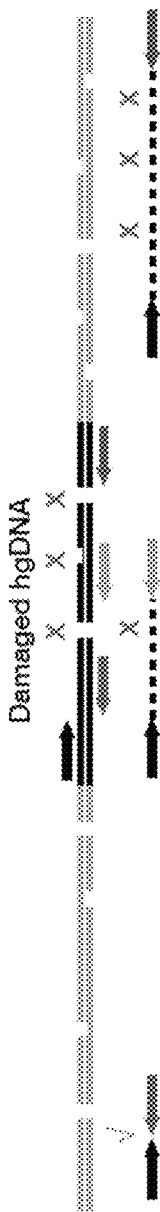

For the determination of the quality of a sample such as a FFPET sample, the ratio of concentrations, measured with different amplicon lengths, is calculated. This is based on the assumption that the priming sites for longer amplicons will be interrupted by the degradation process. FIG. 1 shows schematically the amplification of three amplicons of different length with high quality genomic DNA as template. All three primer pairs give the expected PCR products. FIG. 2 schematically shows the situation for a partially degraded DNA such as FFPET DNA. Only the shortest fragment gives a PCR product because the DNA is interrupted between the two primers for the other two amplicons.

In qPCR, so called cq values are measured for absolute or relative quantification of the original target DNA. A cq value is defined as the amplification cycle, in which the fluorescent signal of a qPCR reaction exceeds a certain fluorescence threshold level. Thus, low cq values indicate a high level of target DNA present in the sample, whereas a high cq values indicate low amounts of target DNA originally present in the sample. Due to the fact that PCR is an exponential amplification reaction, cq values are lowered by increased amount of original target DNA in logarithmic dependency.

The new inventive method for determining the quality of a DNA sample can be carried out in different modes. In one mode, the relative concentration of a first shorter amplicon and a second longer amplicon generated from the same amount of sample DNA is determined directly by determining a cq value for each amplicon and comparing said values. For high quality DNA these determined cq values should be ideally be equal or at least similar. On the other hand, if the DNA is more degraded, the determined concentration of the smaller amplicon will exceed the determined concentration of the longer amplicon and the cq value measured for the shorter amplicon will be much lower than the cp value measured for the longer amplicon.

In another mode, the cq values are first normalized against cq values obtained for a calibrator DNA sample, which is amplified in parallel within the same experiment. In a further mode, the cq values are normalized against a standard curve generated from known amounts of target DNA.

Determination of FFPET Quality Score without a Calibrator Sample

To obtain a sample specific quality value without measuring any standard it is only necessary to measure the cq for two LINE amplicons of different length at the same sample concentration and determine the differences of the cq-values. The difference is a measure for the relative concentration of the two amplicons in this sample. The relative concentration is calculated according to the following formula where $c_{rel}$ is the relative concentration and $cq_x$ and $cq_y$ are the mean cq-values from the qPCR of the indicated amplicon length.

$$c_{rel}=2^{-(cq_x-cq_y)}$$

If $cq_x$ and $cq_y$ are identical or almost identical, then $c_{rel}=1$ or close to 1 and the sample is a high quality sample.

Determination of FFPET Quality Score with a Standard Curve or a Calibrator Sample If standard curves are available for a sample with known good quality (e.g. genomic DNA from blood cells) the Q-score is calculated as the ratio of the concentrations obtained for an unknown sample from these standard curves. Therefore at least two standard curves for to different amplicon length and the values of the unknown sample for the same two amplicons are necessary. The Q-score is then simply calculated by the ratio of the relative concentrations for the two amplicons.

$$Q=c_{long}/c_{short}$$

The determination of the quality score could also be performed by using a calibrator sample. As the absolute difference of concentrations between the unknown and the reference sample is mostly not known the difference of cq's has to be corrected for this. Therefore the cq values for a short amplicon from the sample and the calibrator sample are determined. The difference of the cq's of these amplicons may serve as an measure for the difference of the concentrations of the sample and the calibrator sample. In parallel, the cq values for a longer amplicon from the sample and the calibrator sample are determined. The difference of the cq's of these longer amplicons will serve as a measure for the difference in the DNA quality of the sample and the reference sample. One advantage of this method is that only one standard sample per measurement (e.g. microtiter plate) is needed.

The quality score is calculated as following:

$$\Delta_{cq}=cq_{unknown\_long\ amplicon}-cq_{standard\_long\ amplicon}-(cq_{unknown\_short\ amplicon}-cq_{standard\_short\ amplicon})$$

The relative concentration is then calculated as follows: $c_{rel}=2^{-\Delta cq}$ Determination of Genomic Contamination in cfDNA with and without Using Standards In one embodiment, the degree of contamination of cell free DNA with genomic DNA is determined. Since it has been observed that cell free DNA is more damaged than genomic DNA, differences in amplification of short and long LINE DNA fragments can be used to determine the degree of contamination of cell free DNA by genomic DNA. Thus, without a standard DNA or reference sample, a measure for contamination again may be determined again according to the formula $$c_{ref}=2^{-(cq_x-cq_y)}$$

wherein $cq_x$ and $cq_y$ represent the values for a shorter a longer LINE DNA amplicon. Since every cell free DNA is more damaged as typical cellular DNA, the $cq_x$ and $cq_y$ values of ctDNA are not identical and differ substantially from each other. Therefore, all experiments require the parallel measurement of a ctDNA control sample, for which absence of contamination with cellular DNA has been proven previously. Samples which are contaminated with cellular DNA will then have relative concentration closer to 1 as compared to the control sample In a further embodiment, the present invention provides specific reagents and kits for executing the inventive method. In a first aspect, the present invention provides a first primer pair of amplification primers according to SEQ ID. No: 1 and 2. The present invention also provides a second pair of amplification primers according to SEQ ID No: 3 and 4 The present invention also provides a third pair of amplification primer according to SEQ ID NO: 5 and 2. Two or three of these pairs of amplification primers may constitute a kit for executing the inventive method as disclosed above. Such a kit may further comprise a thermostable DNA polymerase, deoxy-nucleotides and other reagents necessary for performing a PCR amplification reaction.

Example 1

General Set Up

All experiments were performed in a white LightCycler® 480 Multiwell Plate 96 on a LightCycler® instrument according to the manufacturer's instructions, using the FastStart Essential DNA Green Master kit (Roche Id No. 06924204001) for setting up the PCR amplification reaction.

A first primer pair according to SEQ ID. No: 1 and 2 was used to amplify a 66 bp LINE amplicon, a second primer pair according to SEQ ID. No: 3 and 4 was used to amplify a 161 bp LINE amplicon and a third primer pair according to SEQ ID NO: 5 and 2 was used to amplify a 330 bp LINE amplicon. For amplification, a primer concentration of 0.4 µM each was used.

Five microliter of the diluted DNA sample was distributed to appropriate wells of a Multiwell Plate. After this the mastermix was added. Experiments were always done in triplicates.

The thermocycling protocol was as follows:

| Temperature | Time | Ramp | Cycles |
|---|---|---|---|
| 95° C. | 600 sec | 4.4° C./s | 1 |
| 95° C. | 10 sec | 4.4° C./s | 40 |
| 60° C. | 30 sec | 2.2° C./s | |
| 72° C. | 30 sec | 4.4° C./s | |

The data are analysed using the standard analysis of the LightCycler® 96 SW 1.1 software and the results were exported into an Excel sheet were remaining calculations were done. The QC-ratio was calculated as the quotient of concentrations of the indicated amplicons.

Example 2

Determination of FFPET Quality Score without an Internal Standard Sample

Experimental conditions were as disclosed in example 1. 5 DNA and 5 clinical samples with an unknown amount of DNA were used. Mean absolute concentration values for the clinical samples were determined by means of creating a typical standard curve first. The Δcq values were created by subtracting the measured cq from the cq values as determined by the standard curve. The results are shown in the following table.

| Assay | Mean Conc. | Cq Mean | Cq Error | QC-ratio conc 191/conc 66 | QC-ratio conc 330/conc 66 | $\Delta_{cq}$ 191-66 | $\Delta_{cq}$ 333-66 | $\Delta_{cq}$ 191-330 |
|---|---|---|---|---|---|---|---|---|
| 1_66 bp | 7.2 | 17.95 | 0.04 | | | | | |
| 2_ 66 bp | 26.0 | 16.13 | 0.07 | | | | | |
| 3_66 bp | 8.3 | 17.75 | 0.03 | | | | | |
| 4_66 bp | 65.3 | 14.82 | 0.06 | | | | | |
| 5_66 bp | 23.1 | 16.3 | 0.15 | | | | | |
| Standard 256 pg/µL_191 bp | 251.8 | 11.64 | 0.04 | 0.99 | | 2.36 | | |
| Standard 64 pg/µL_ 191 bp | 64.8 | 13.59 | 0.03 | 1.00 | | 2.35 | | |
| Standard 16 pg/µL_ 191 bp | 16.2 | 15.57 | 0.04 | 1.01 | | 2.36 | | |
| Standard 4 pg/µL_ 191 bp | 4.0 | 17.58 | 0.03 | 1.02 | | 2.36 | | |
| Standard 1 pg/µL_ 191 bp | 1.0 | 19.58 | 0.01 | 0.98 | | 2.25 | | |
| 1_191 bp | 0.3 | 21.35 | 0.1 | 0.04 | | 0.09 | | |
| 2_ 191 bp | 0.4 | 20.76 | 0.05 | 0.02 | | 0.04 | | |
| 3_191 bp | 0.8 | 19.84 | 0.03 | 0.10 | | 0.23 | | |
| 4_191 bp | 20.6 | 15.23 | 0.03 | 0.32 | | 0.75 | | |
| 5_191 bp | 4.9 | 17.3 | 0.02 | 0.21 | | 0.50 | | |
| Standard 256 pg/µL_330 bp | 257.7 | 10.48 | 0.05 | | 1.01 | | 5.278 | 2.235 |
| Standard 64 pg/µL_ 330 bp | 65.4 | 12.49 | 0.01 | | 1.01 | | 5.028 | 2.144 |

-continued

| Assay | Mean Conc. | Cq Mean | Cq Error | QC-ratio conc 191/ conc 66 | QC-ratio conc 330/ conc 66 | $\Delta_{cq}$ 191-66 | $\Delta_{cq}$ 333-66 | $\Delta_{cq}$ 191-330 |
|---|---|---|---|---|---|---|---|---|
| Standard 16 pg/µL 330 bp | 15.4 | 14.61 | 0.02 | | 0.96 | | 4.595 | 1.945 |
| Standard 4 pg/µL 330 bp | 4.0 | 16.57 | 0.05 | | 1.03 | | 4.757 | 2.014 |
| Standard 1 pg/µL 330 bp | 1.0 | 18.6 | 0.03 | | 1.00 | | 4.438 | 1.972 |
| 1_330 bp | 0.01 | 25.44 | 0.07 | | 0.001 | | 0.006 | 0.059 |
| 2_330 bp | 0.01 | 25.16 | 0.05 | | 0.0004 | | 0.002 | 0.047 |
| 31_330 bp | 0.1 | 22.14 | 0.04 | | 0.01 | | 0.048 | 0.203 |
| 4_330 bp | 6.8 | 15.8 | 0.02 | | 0.10 | | 0.507 | 0.674 |
| 5_330 bp | 1.1 | 18.48 | 0.08 | | 0.05 | | 0.221 | 0.441 |

The results indicate that the QC ratios obtained were always close to 1 for the amplified standard DNA, whereas different values were obtained for the clinical samples.

Example 3

Determination of FFPET quality score with a calibrator sample

Three calibrator samples, having 64 pg/µl, 16 pg/µl, and 4 pg/µl genomic DNA, respectively, were used. The data obtained in example 2 were further processed according to the formula $$\Delta_{cq} = cq_{unknown\_long\ amplicon} - cq_{standard\_long\ amplicon} - (cq_{unknown\_short\ amplicon} - cq_{standard\_short\ amplicon})$$

The values obtained are shown in the following table:

| Assay | Mean Conc. | Cq Mean | Cq Error | QC-ratio conc 191/ conc 66 | QC-ratio conc 330/ conc 66 | $\Delta_{cq}$ 64 pg/µl | $\Delta_{cq}$ 16 pg/µl | $\Delta_{cq}$ 4 pg/µl |
|---|---|---|---|---|---|---|---|---|
| Standard 256 pg/µl_66 bp | 254.3 | 12.88 | 0.08 | | | | | |
| Standard 64 pg/µl_66 bp | 65.0 | 14.82 | 0.05 | | | | | |
| Standard 16 pg/µl_66 bp | 16.1 | 16.81 | 0.01 | | | | | |
| Standard 4 pg/µl_66 bp | 3.9 | 18.82 | 0.07 | | | | | |
| Standard 1 pg/µl_66 bp | 1.0 | 20.75 | 0.02 | | | | | |
| 1_66 bp | 7.2 | 17.95 | 0.04 | | | | | |
| 2_66 bp | 26.0 | 16.13 | 0.07 | | | | | |
| 3_66 bp | 8.3 | 17.75 | 0.03 | | | | | |
| 4_66 bp | 65.3 | 14.82 | 0.06 | | | | | |
| 5_66 bp | 23.1 | 16.3 | 0.15 | | | | | |
| Standard 256 pg/µl_191 bp | 251.8 | 11.64 | 0.04 | 0.99 | | −0.01 | 0 | 0 |
| Standard 64 pg/µl_191 bp | 64.8 | 13.59 | 0.03 | 1.00 | | 0 | 0.01 | 0.01 |
| Standard 16 pg/µl_191 bp | 16.2 | 15.57 | 0.04 | 1.01 | | −0.01 | 0 | 0 |
| Standard 4 pg/µl_191 bp | 4.0 | 17.58 | 0.03 | 1.02 | | −0.01 | 0 | 0 |
| Standard 1 pg/µl_191 bp | 1.0 | 19.58 | 0.01 | 0.98 | | 0.06 | 0.07 | 0.07 |
| 1_191 bp | 0.3 | 21.35 | 0.1 | 0.04 | | 4.63 | 4.64 | 4.64 |
| 2_191 bp | 0.4 | 20.76 | 0.05 | 0.02 | | 5.86 | 5.87 | 5.87 |
| 3_191 bp | 0.8 | 19.84 | 0.03 | 0.10 | | 3.32 | 3.33 | 3.33 |
| 4_191 bp | 20.6 | 15.23 | 0.03 | 0.32 | | 1.64 | 1.65 | 1.65 |
| 5_191 bp | 4.9 | 17.3 | 0.02 | 0.21 | | 2.23 | 2.24 | 2.24 |
| Standard 256 pg/µl_330 bp | 257.7 | 10.48 | 0.05 | | 1.01 | −0.07 | −0.2 | −0.15 |
| Standard 64 pg/µl_330 bp | 65.4 | 12.49 | 0.01 | | 1.01 | 0 | −0.13 | −0.08 |

-continued

| Assay | Mean Conc. | Cq Mean | Cq Error | QC-ratio conc 191/ conc 66 | QC-ratio conc 330/ conc 66 | $\Delta_{cq}$ 64 pg/µl | $\Delta_{cq}$ 16 pg/µl | $\Delta_{cq}$ 4 pg/µl |
|---|---|---|---|---|---|---|---|---|
| Standard 16 pg/µL_ 330 bp | 15.4 | 14.61 | 0.02 | | 0.96 | 0.13 | 0 | 0.05 |
| Standard 4 pg/µL_ 330 bp | 4.0 | 16.57 | 0.05 | | 1.03 | 0.08 | −0.05 | 0 |
| Standard 1 pg/µL_ 330 bp | 1.0 | 18.6 | 0.03 | | 1.00 | 0.18 | 0.05 | 0.1 |
| 1_330 bp | 0.01 | 25.44 | 0.07 | | 0.001 | 9.82 | 9.69 | 9.74 |
| 2_ 330 bp | 0.01 | 25.16 | 0.05 | | 0.0004 | 11.36 | 11.23 | 11.28 |
| 31_330 bp | 0.1 | 22.14 | 0.04 | | 0.01 | 6.72 | 6.59 | 6.64 |
| 4_330 bp | 6.8 | 15.8 | 0.02 | | 0.10 | 3.31 | 3.18 | 3.23 |
| 5_330 bp | 1.1 | 18.48 | 0.08 | | 0.05 | 4.51 | 4.38 | 4.43 |

Again, the results indicate that the QC ratios obtained are always close to 1 for the amplified standard DNA, whereas different values were obtained for the clinical samples.

Example 4

Measurement of Contamination of Cell Free DNA with Genomic DNA without a Calibrator Sample As already shown in example 2 it is possible to determine the relative concentration of the different amplicons by simply subtracting the cq-values for the different amplicons. Therefore it is merely necessary to measure the assays with the same sample concentration.

For this experiment, cell free DNA was prepared as follows: Human whole blood was centrifuged for 10 minutes at 4000 g. The supernatant was carefully removed leaving the buffy coat untouched and subjected to a second centrifugation for 5 minutes at 4000 g. Again, the supernatant was carefully removed and subjected to further analysis. To check for the variability, aliquots from the same cell free DNA (ctDNA) sample were spiked with 5% and 25% genomic DNA respectively.

Pure cfDNA without contamination of genomic DNA from blood cells was obtained by double centrifugation for 10 minutes at 4000 g (each with careful removal of the supernatant)

| | 66 bp | | 191 bp | | | 330 bp | | |
|---|---|---|---|---|---|---|---|---|
| Sample Name | Cq Mean | Cq Error | Cq Mean | Cq Error | Crel cq191/ cq66 | Cq Mean | Cq Error | Crel cq330/ cq66 |
| ctDNA_1 | 16.58 | 0.02 | 16.99 | 0.04 | 0.75 | 16.88 | 0.07 | 0.81 |
| ctDNA_2 | 16.60 | 0.03 | 16.99 | 0.05 | 0.76 | 16.85 | 0.03 | 0.84 |
| ctDNA_3 | 16.61 | 0.04 | 17.08 | 0.08 | 0.72 | 16.92 | 0.06 | 0.81 |
| ctDNA_4 | 18.67 | 0.36 | 19.25 | 0.18 | 0.67 | 19.26 | 0.02 | 0.66 |
| ctDNA_5 | 18.77 | 0.03 | 19.43 | 0.03 | 0.63 | 19.21 | 0.03 | 0.74 |
| ctDNA_6 | 18.78 | 0.01 | 19.46 | 0.07 | 0.62 | 19.21 | 0.03 | 0.74 |
| ctDNA_7 | 18.75 | 0.03 | 19.43 | 0.05 | 0.62 | 19.25 | 0.05 | 0.71 |
| ctDNA_8 | 18.80 | 0.05 | 19.56 | 0.04 | 0.59 | 19.18 | 0.05 | 0.77 |
| ctDNA_9 | 16.51 | 0.01 | 16.96 | 0.04 | 0.73 | 16.78 | 0.02 | 0.83 |
| ctDNA_10 | 16.37 | 0.02 | 16.92 | 0.03 | 0.68 | 16.91 | 0.04 | 0.69 |
| ctDNA_11 | 16.44 | 0.01 | 17.04 | 0.06 | 0.66 | 17.11 | 0.10 | 0.63 |
| ctDNA_12 | 16.54 | 0.01 | 16.94 | 0.06 | 0.76 | 16.78 | 0.02 | 0.85 |
| ctDNA_13 | 16.39 | 0.02 | 16.97 | 0.04 | 0.67 | 17.00 | 0.03 | 0.66 |
| ctDNA_14 | 16.44 | 0.04 | 17.05 | 0.05 | 0.66 | 17.15 | 0.02 | 0.61 |
| ctDNA_15 | 16.54 | 0.04 | 16.94 | 0.03 | 0.76 | 16.83 | 0.07 | 0.82 |
| ctDNA_16 | 16.41 | 0.02 | 16.95 | 0.02 | 0.69 | 17.02 | 0.05 | 0.66 |
| ctDNA_17 | 16.46 | 0.02 | 17.07 | 0.05 | 0.66 | 17.13 | 0.1 | 0.63 |
| ctDNA_1 + 5% gDNA | 16.51 | 0.03 | 16.87 | 0.01 | 0.78 | 16.63 | 0.03 | 0.92 |
| ctDNA_2 + 5% gDNA | 16.56 | 0.03 | 16.87 | 0.01 | 0.81 | 16.65 | 0.03 | 0.94 |
| ctDNA_3 + 5% gDNA | 16.64 | 0.06 | 16.92 | 0.04 | 0.82 | 16.66 | 0.10 | 0.99 |
| ctDNA_4 + 5% gDNA | 18.62 | 0.24 | 18.85 | 0.14 | 0.85 | 18.64 | 0.08 | 0.99 |
| ctDNA_5 + 5% gDNA | 18.75 | 0.10 | 19.02 | 0.03 | 0.83 | 18.65 | 0.02 | 1.07 |
| ctDNA_6 + 5% gDNA | 18.75 | 0.09 | 19.08 | 0.07 | 0.80 | 18.64 | 0.02 | 1.08 |
| ctDNA_7 + 5% gDNA | 18.69 | 0.01 | 19.06 | 0.05 | 0.77 | 18.70 | 0.01 | 0.99 |
| ctDNA_8 + 5% gDNA | 18.75 | 0.01 | 19.09 | 0.03 | 0.79 | 18.62 | 0.07 | 1.09 |

|  | | 66 bp | | 191 bp | | | 330 bp | | |
|---|---|---|---|---|---|---|---|---|---|
| Sample Name | | Cq Mean | Cq Error | Cq Mean | Cq Error | Crel cq191/cq66 | Cq Mean | Cq Error | Crel cq330/cq66 |
| ctDNA_9 + 5% gDNA | | 16.48 | 0.01 | 16.82 | 0.04 | 0.79 | 16.55 | 0.04 | 0.95 |
| ctDNA_10 + 5% gDNA | | 16.39 | 0.01 | 16.77 | 0.06 | 0.77 | 16.60 | 0.08 | 0.86 |
| ctDNA_11 + 5% gDNA | | 16.55 | 0.12 | 16.78 | 0.01 | 0.85 | 16.62 | 0.16 | 0.95 |
| ctDNA_12 + 5% gDNA | | 16.51 | 0.02 | 16.83 | 0.03 | 0.80 | 16.49 | 0.02 | 1.01 |
| ctDNA_13 + 5% gDNA | | 16.41 | 0.03 | 16.81 | 0.03 | 0.76 | 16.69 | 0.02 | 0.82 |
| ctDNA_14 + 5% gDNA | | 16.45 | 0.01 | 16.77 | 0.05 | 0.80 | 16.77 | 0.03 | 0.80 |
| ctDNA_15 + 5% gDNA | | 16.52 | 0.02 | 16.82 | 0.07 | 0.81 | 16.59 | 0.06 | 0.95 |
| ctDNA_16 + 5% gDNA | | 16.47 | 0.04 | 16.84 | 0.02 | 0.77 | 16.73 | 0.03 | 0.84 |
| ctDNA_17 + 5% gDNA | | 16.16 | 0.53 | 16.86 | 0.04 | 0.62 | 16.81 | 0.04 | 0.64 |
| ctDNA_1 + 25% gDNA | | 16.60 | 0.03 | 16.57 | 0.02 | 1.02 | 15.95 | 0.03 | 1.57 |
| ctDNA_2 + 25% gDNA | | 16.61 | 0.03 | 16.51 | 0.04 | 1.07 | 15.89 | 0.03 | 1.65 |
| ctDNA_3 + 25% gDNA | | 16.67 | 0.01 | 16.67 | 0.01 | 1.00 | 15.98 | 0.03 | 1.61 |
| ctDNA_4 + 25% gDNA | | 18.20 | 0.20 | 17.86 | 0.14 | 1.27 | 17.40 | 0.06 | 1.74 |
| ctDNA_5 + 25% gDNA | | 18.30 | 0.05 | 18.00 | 0.06 | 1.23 | 17.37 | 0.01 | 1.91 |
| ctDNA_6 + 25% gDNA | | 18.38 | 0.03 | 17.87 | 0.28 | 1.42 | 17.40 | 0.10 | 1.97 |
| ctDNA_7 + 25% gDNA | | 18.31 | 0.04 | 18.05 | 0.03 | 1.20 | 17.50 | 0.02 | 1.75 |
| ctDNA_8 + 25% gDNA | | 18.42 | 0.07 | 18.16 | 0.07 | 1.20 | 17.32 | 0.07 | 2.14 |
| ctDNA_9 + 25% gDNA | | 16.51 | 0.04 | 16.35 | 0.07 | 1.12 | 15.83 | 0.07 | 1.60 |
| ctDNA_10 + 25% gDNA | | 16.44 | 0.02 | 16.32 | 0.04 | 1.09 | 15.84 | 0.02 | 1.52 |
| ctDNA_11 + 25% gDNA | | 16.50 | 0.08 | 16.34 | 0.06 | 1.12 | 15.82 | 0.12 | 1.60 |
| ctDNA_12 + 25% gDNA | | 16.54 | 0.02 | 16.36 | 0.01 | 1.13 | 15.76 | 0.02 | 1.72 |
| ctDNA_13 + 25% gDNA | | 16.43 | 0.01 | 16.37 | 0.02 | 1.04 | 15.87 | 0.02 | 1.47 |
| ctDNA_14 + 25% gDNA | | 16.44 | 0.03 | 16.38 | 0.02 | 1.04 | 15.91 | 0.08 | 1.44 |
| ctDNA_15 + 25% gDNA | | 16.54 | 0.03 | 16.4 | 0.04 | 1.10 | 15.79 | 0.03 | 1.68 |
| ctDNA_16 + 25% gDNA | | 16.43 | 0.04 | 16.4 | 0.01 | 1.02 | 15.88 | 0.04 | 1.46 |
| ctDNA_17 + 25% gDNA | | 16.46 | 0.07 | 16.41 | 0.04 | 1.04 | 15.9 | 0.03 | 1.47 |

For the 3×17 experiments, the Average, Minimum and Maximum Values were calculated as follows:

|  |  | crel cq191/cq66 | crel cq330/cq66 |
|---|---|---|---|
| ctDNA | Minimum | 0.59 | 0.61 |
|  | Maximum | 0.76 | 0.85 |
|  | Mean | 0.68 | 0.73 |
| ctDNA + 5% gDNA | Minimum | 0.62 | 0.64 |
|  | Maximum | 0.85 | 1.09 |
|  | Mean | 0.79 | 0.94 |
| ctDNA + 25% gDNA | Minimum | 1.00 | 1.44 |
|  | Maximum | 1.42 | 2.14 |
|  | Mean | 1.12 | 1.67 |

These data clearly demonstrate that contamination with cellular DNA can be detected without any standard or calibrator sample. However, there is an overlap between the maximum and minimum values for the data obtained without a spike and 5% spike-in concentrations. Therefore the use of a control sample, which has been proven previously to contain no genomic contamination, is mandatory.

Example 5

Measurement of Contamination of Cell Free DNA with Genomic DNA with a Calibrator Sample For this experiment, the setup of the reactions was similar to the approach described for example 4 above. In order to check for the robustness of the method three different cfDNA extractions from three different healthy donors were used. Three repeats of the experiment were performed with each data point in triplicate. A sample which has no genomic contamination as internal reference was used for calibration as a reference sample.

| Sample Name | 66bp Cq Mean | 191bp Cq Mean | 191bp Δ cqcor191 | 330bp Cq Mean | 330bp Δ cqcor330 |
|---|---|---|---|---|---|
| ctDNA_49400_1 | 16.51 | 16.96 | | 16.78 | |
| ctDNA_49384_1 | 16.37 | 16.92 | | 16.91 | |
| ctDNA_49414_1 | 16.44 | 17.04 | | 17.11 | |
| ctDNA_49400_2 | 16.54 | 16.94 | | 16.78 | |
| ctDNA_49384_2 | 16.39 | 16.97 | | 17 | |
| ctDNA_49414_2 | 16.44 | 17.05 | | 17.15 | |
| ctDNA_49400_3 | 16.54 | 16.94 | | 16.83 | |
| ctDNA_49384_3 | 16.41 | 16.95 | | 17.02 | |
| ctDNA_49414_3 | 16.46 | 17.07 | | 17.13 | |
| 49400_1 (+5% gDNA) | 16.48 | 16.82 | −0.11 | 16.55 | −0.2 |
| 49384_1 (+5% gDNA) | 16.39 | 16.77 | −0.17 | 16.6 | −0.33 |
| 49414_1 (+5% gDNA) | 16.55 | 16.78 | −0.37 | 16.62 | −0.6 |
| 49400_2 (+5% gDNA) | 16.51 | 16.83 | −0.08 | 16.49 | −0.26 |
| 49384_2 (+5% gDNA) | 16.41 | 16.81 | −0.18 | 16.69 | −0.33 |
| 49414_2 (+5% gDNA) | 16.45 | 16.77 | −0.29 | 16.77 | −0.39 |
| 49400_3 (+5% gDNA) | 16.52 | 16.82 | −0.1 | 16.59 | −0.22 |
| 49384_3 (+5% gDNA) | 16.47 | 16.84 | −0.17 | 16.73 | −0.35 |
| 49414_3 (+5% gDNA) | 16.46 | 16.86 | −0.21 | 16.81 | −0.32 |
| 49400_1 (+25% gDNA) | 16.51 | 16.35 | −0.61 | 15.83 | −0.95 |
| 49384_1 (+25% gDNA) | 16.44 | 16.32 | −0.67 | 15.84 | −1.14 |
| 49414_1 (+25% gDNA) | 16.5 | 16.34 | −0.76 | 15.82 | −1.35 |
| 49400_2 (+25% gDNA) | 16.54 | 16.36 | −0.58 | 15.76 | −1.02 |
| 49384_2 (+25% gDNA) | 16.43 | 16.37 | −0.64 | 15.87 | −1.17 |
| 49414_2 (+25% gDNA) | 16.44 | 16.38 | −0.67 | 15.91 | −1.24 |
| 49400_3 (+25% gDNA) | 16.54 | 16.4 | −0.54 | 15.79 | −1.04 |
| 49384_3 (+25% gDNA) | 16.43 | 16.4 | −0.57 | 15.88 | −1.16 |
| 49414_3 (+25% gDNA) | 16.46 | 16.41 | −0.66 | 15.9 | −1.23 |

As shown in the table, comparison of the corrected Δ cq values allowed the reliable detection of genomic contamination in cfDNA already at the 5% level.

The invention claimed is:

1. A method of measuring quality of cell free DNA in a sample comprising the steps of
   a) providing (i) a DNA sample comprising cell free DNA and cellular DNA, and (ii) a control sample which has been proven previously to contain no genomic contamination,
   b) providing a first pair of amplification primers comprising SEQ ID Nos: 1 and 2, which is capable of generating a first amplicon from a LINE sequence that has a size of less than 80 bp,
   c) providing a second pair of amplification primers comprising SEQ ID Nos: 3 and 4 which is capable of generating a second amplicon from a LINE sequence that has a size of more than 160 bp,
   d) providing a third pair of amplification primers comprising SEQ ID Nos: 5 and 2 which is capable of generating a third amplicon from a LINE sequence that has a size of more than 300 bp,
   e) performing a qPCR with the first and the second pair of amplification primers and determining cq values for the first and the second generated amplicons in the DNA sample and the control sample,
   f) determining the relative concentrations of said amplicons in the DNA sample and the control sample using the formula $$c_{rel} = 2^{-(cqx-cqy)}$$

where cqx is cq of the second amplicon and cqy is cq of the first amplicon, and
   g) determining the quality of the cell free DNA in the DNA sample based on a proximity of $c_{rel}$ to 1, wherein if the DNA sample is contaminated with cellular DNA, the $c_{rel}$ will be closer to 1 as compared to the control sample.

2. A method according to claim 1, wherein the cq values obtained in step d) are normalized using a calibrator sample whereby normalized $cqx'' = cqx - cqx_{calibrator}$ and normalized cqy is $cqy'' = cqy - cqy_{calibrator}$ and $c_{rel}$ in step e) is calculated using the normalized cq values.

3. The method according to claim 1, wherein the sample is an FFPET sample.

4. The method according to claim 1, wherein the sample is a cell free DNA sample.

* * * * *